United States Patent [19]

Bringer-Meyer et al.

[11] Patent Number: 5,017,485
[45] Date of Patent: May 21, 1991

[54] PROCESS FOR OBTAINING SORBITOL AND GLUCONIC ACID BY FERMENTATION, AND CELL MATERIAL SUITABLE FOR THIS PURPOSE

[75] Inventors: Stephanie Bringer-Meyer, Krefeld; Hermann Sahm, Juelich, both of Fed. Rep. of Germany

[73] Assignee: Forschungszentrum Juelich GmbH, Fed. Rep. of Germany

[21] Appl. No.: 448,334

[22] Filed: Dec. 11, 1989

[30] Foreign Application Priority Data

Dec. 10, 1988 [DE] Fed. Rep. of Germany ....... 3841702

[51] Int. Cl.$^5$ .......................... C12P 7/58; C12P 7/18; C07C 31/26; C07C 59/105
[52] U.S. Cl. ..................... 435/158; 435/137; 435/146; 435/252.1; 435/259; 435/822
[58] Field of Search ............... 435/158, 137, 146, 822, 435/252.1, 259

[56] References Cited

U.S. PATENT DOCUMENTS 4,755,467 7/1988 Scopes et al. ...................... 435/125

OTHER PUBLICATIONS

Felix, "Permeabilized Cells," Analytical Biochemistry 120, 1982, pp. 211-234.

*Primary Examiner*—Herbert J. Lilling
*Attorney, Agent, or Firm*—Foley & Lardner

[57] ABSTRACT

A process is disclosed for obtaining sorbitol and gluconic acid, or gluconate, by fermentation in aqueous glucose/fructose mixtures. *Zymomonas mobilis* cells are used which have been permeabilized by the freeze technique and which have preferably been obtained by freezing cell centrifugates of pH 6 to 7 at about −20° C., and thawing at room temperature. Cell concentrations of 20 to 60 g of cell dry matter of permeabilized cells/l are preferably used for the fermentation. By using cells which have been permeabilized by freezing and thawing, a considerably higher conversion rate of glucose/fructose into sorbitol and gluconic acid, or gluconate, is achieved.

7 Claims, No Drawings

PROCESS FOR OBTAINING SORBITOL AND GLUCONIC ACID BY FERMENTATION, AND CELL MATERIAL SUITABLE FOR THIS PURPOSE

BACKGROUND OF THE INVENTION

The present invention relates to a process for obtaining sorbitol and gluconic acid, or gluconate, by fermentation in the presence of permeabilized *Zymomonas mobilis* cells, starting from aqueous glucose/fructose mixtures, and to a permeabilized cell material suitable for this purpose.

It is known that sorbitol and gluconic acid, or gluconate, are formed enzymatically in aqueous glucose/fructose mixtures with the aid of glucose dehydrogenase and sorbitol dehydrogenase in the simultaneous presence of cofactors. A prerequisite of this process is the continuous addition or regeneration of the cofactors.

A process has therefore been developed (U.S. Pat. No. 4,755,467) for the microbial conversion of glucose and fructose in aqueous solution with the aid of bacteria containing glucose/fructose transhydrogenase, in particular of *Zymomonas mobilis*. In this process demineralized cell-free extracts, or immobilized cells, or non-growing cells washed with phosphate-free buffer are used which may have been rendered permeable, for which purpose a toluene treatment was exemplified. An alternative object is the formation and application of gluconate kinase-negative mutants.

SUMMARY OF THE INVENTION

It is therefore an object of the present invention to provide an improved fermentation process for production of sorbitol and gluconic acid, or gluconate, from aqueous glucose/fructose mixtures.

It is a further object of the present invention to provide permeabilized cell material that can be used to ferment aqueous glucose/fructose mixtures.

In accordance with these and other objects according to the invention there is provided a process for obtaining sorbitol and gluconic acid, or gluconate, comprising the steps of:

permeabilizing *Zymomonas mobilis* cells by the freezing technique, and fermentating an aqueous glucose/fructose mixture with the permeabilized *Zymomonas mobilis* cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Surprisingly, it has now been found that the conversion of glucose/fructose into sorbitol and gluconic acid, or gluconate proceeds at a considerably higher yield when cells are employed which have been permeabilized by freezing and thawing.

Accordingly, the process according to the invention comprises the use of cells which have been permeabilized by the freeze technique.

Even though the freeze technique as a means for permeabilizing cells (for example *E. coli*) is mentioned as one of many techniques, in Hansruedi *Felix. Anal. Biochem.* 120: 211–234 (1982); (see, in particular, p. 221), it was entirely unexpected that a very considerable improvement could be achieved in a process for producing sorbitol and gluconic acid, or gluconate, by using *Z. mobilis* cells permeabilized by a freezing technique.

Preferably, the cells which are to be permeabilized by freezing and thawing are suspended in dilute buffer solution of pH 6 to 7 after they have been separated from the culture medium, and in this form they are frozen at about $-20°$ C. and subsequently thawed at room temperature. The buffer used is, in particular, sodium citrate buffer of pH 6.5, in which the biomass is suspended in amounts of, in particular, about 50–150 g of cell dry matter/l. Expediently, the biomass can be washed once or several times with citrate buffer before it is frozen.

The freezing temperature should be in a range where sufficient seed water crystals have already formed. In this context, it must be taken into account that the entire biomass does not instantaneously reach the freezer temperature, its mean temperature approaching the freezer temperature only more or less rapidly. Depending on the geometry of the biomass, about $-10°$ C. is to be regarded as the upper limit of the freezing temperature. Good results were achieved when suspension tubes (diameter 2.5 cm, length 4.5 cm, wall material polyethylene) were frozen in a freezer at about $-20°$ C. It is also possible to work at lower temperatures, for example, cooling can be effected down to about $-30°$ C. and below.

Thawing can be effected simply at room temperature, by removing the samples from the freezer, or, alternatively, by transferring the samples to a water bath at a suitable temperature in order to somewhat accelerate the thawing process, with the result that a certain improvement of the usefulness of the permeabilized cells for the production of sorbitol and gluconic acid is achieved.

Such permeabilized cell materials can be produced, stocked and marketed in analogy to, say, enzyme preparations.

Glucose/fructose mixtures used for obtaining sorbitol and gluconic acid are, in particular, aqueous glucose/fructose mixtures of a concentration of, in each case, about 100–270 g/l, preferably about 200 g/l of each of the hexoses. In particular, the cell concentration is in the range of about 20–50 g of cell dry matter/l, preferably at approximately 40 g of cell dry matter/l. The pH chosen can be in the range of 5.5–7.0 and is preferably at 6.5, the pH preferably being monitored by titration with 2 M $Na_2CO_3$ solution.

The process is desirably carried out in a buffered solution, in particular in sodium citrate buffer (0.1 M, pH 6.5), or using other buffer solutions which buffer in the pH range mentioned, and which are phosphate-free.

The temperature is advantageously between about 30° C. and 42° C., and preferably at about 39° C.

The invention is explained more fully with reference to the following illustrative examples.

EXAMPLE 1

Obtaining permeabilized cells.
Cell culture: pH-static in a fermenter
Substrate: 150 g/l of sucrose
Medium (g/100 ml of $H_2O$)
Yeast extract: 0.5
$KH_2PO_4$: 0.1
$(NH_4)_2SO_4$: 0.1
$MgSO_4 \times 7\ H_2O$: 0.05
pH 5.0
Growth period: about 16 hours Cell harvest: At an optical density ($OD_{550\ nm}$) of 13.4, the suspension is centrifuged for 20 minutes at 10,000×g. The cells are then resuspended in 0.1 M sodium citrate buffer, pH 6.5, and the suspension is centrifuged. The cells are taken up in citrate buffer (about 120 g of cell dry matter/l), and the suspension is frozen at $-20°$ C. The cells are thawed at room temperature, centrifuged for 20 minutes at 48,000×g and resuspended in 0.1 M sodium citrate buffer, pH 6.5. The suspension is centrifuged for 10 minutes at 48,000×g. The cells are resuspended in sodium citrate buffer, pH 6.5, cell concentration about 30 g of cell dry matter/l.

EXAMPLE 2

Obtaining sorbitol and gluconic acid with the aid of the permeabilized cells.

Glucose, fructose and permeabilized *Z. mobilis* cells were charged to a fermentation in the following concentrations:
Glucose: 234 g/l (1.3 M)
Fructose: 234 g/l (1.3 M)
Cell concentration: 43 g of cell dry matter/l Fermentation was carried out in sodium citrate buffer (0.1 M, pH 6.5). The pH in the fermentation vessel was adjusted to 6.5 and maintained by titration with 2 M $Na_2CO_3$ solution. The temperature in the reactor was maintained at 39° C.

After a reaction time of 5 hours, the following concentrations were measured:
Sorbitol: 233 g/l (1.28 M)
Gluconic acid: 247 g/l (1.26 M)
Fructose: 3.6 g/l (0.02 M)
Glucose: 7.2 g/l (0.04 M)

What is claimed is:

1. A fermentation process, comprising the steps of:
   freezing and thawing *Zymomonas mobilis* cells to produce permeabilized *Zymomonas mobilis* cells, and
   fermenting an aqueous glucose/fructose mixture with the permeabilized *Zymomonas mobilis* cells whereby at least 97% of the fructose is converted to sorbitol within five hours.

2. A process as claimed in claim 1, wherein the permeabilized cells are obtained by centrifuging *Z. mobilis* cells, resuspending the centrifuged cells in dilute buffer solution of pH 6 to 7, freezing the resuspended cells at about $-20°$ C., and thawing the frozen resuspended cells at room temperature.

3. A process as claimed in claim 2, wherein cell centrifugates contain 50 to 150 g of cell dry matter/l and wherein the cell centrifugates are resuspended in 0.1 M sodium citrate buffer of pH 6.5.

4. A process as claimed in claim 3, wherein the centrifuged cells are repeatedly resuspended prior to freezing.

5. A process as claimed in claim 4, wherein the permeabilized cells are resuspended at least once in citrate buffer.

6. A process as claimed in claim 1, wherein the fermentation is carried out at cell concentrations of permeabilized cells of 20 to 60 g of cell dry matter/l.

7. Permeabilized cell material of *Zymomonas mobilis*, consisting of cells which have been permeabilized by the freeze technique.

* * * * *